United States Patent [19]

Stanley et al.

[11] Patent Number: 4,803,218
[45] Date of Patent: Feb. 7, 1989

[54] 3-AMINOALKYL-1H-INDOLE-5-UREA AND AMIDE DERIVATIVES

[75] Inventors: Kerry G. Stanley, Lansdale; Winston Ho, Hatfield, both of Pa.

[73] Assignee: McNeilab, Inc., Spring House, Pa.

[21] Appl. No.: 427,024

[22] Filed: Sep. 29, 1982

[51] Int. Cl.<sup>4</sup> ................. C07D 209/16; C07D 401/14; C07D 401/12; A61K 31/40

[52] U.S. Cl. .................... 514/414; 548/504; 548/507; 548/467; 548/468; 546/273; 514/415

[58] Field of Search ........................ 548/503, 504, 507; 544/509; 514/415, 414

[56] References Cited

U.S. PATENT DOCUMENTS

| | | | |
|---|---|---|---|
| 2,890,223 | 6/1959 | Woolley et al. | 548/504 |
| 2,995,566 | 8/1961 | Sletzinger et al. | 548/504 |
| 2,995,567 | 8/1961 | Sarett et al. | 548/504 |
| 3,182,071 | 5/1965 | Shavel et al. | 548/504 |
| 3,472,870 | 10/1969 | Larsen et al. | 548/504 |
| 3,489,429 | 1/1970 | Herbst | 548/504 |
| 4,064,255 | 12/1977 | Champsein et al. | 548/504 |
| 4,252,803 | 2/1981 | Webb | 548/504 |

OTHER PUBLICATIONS

Boltze, et al., "Substituted Indole-3-Acetoxy-Alkylsulfonic Acid Salts," *Chem. Abst.* 91:5110z (1979).
Glennon and Gessner, "Serotonin Receptor Binding . . . ," *Chem Abst.* 90:132591 (1979).
Coates, et al., "Indole Derivatives . . . ," *Chem. Abst.* 97:6148d (1982).
McOnie, *Protective Groups in Organic Chem.* Plenum Press, New York, (1973) pp. 48, 49, 76, 77, 80, and 81.
Goodman, et al., *Pharmacological Basis of Therapeutics,* Macmillan, New York (1965) pp. 651–653.

*Primary Examiner*—Mark L. Berch
*Attorney, Agent, or Firm*—David J. Levy

[57] ABSTRACT

Compounds useful as antihypertensive agents which are 3-aminoalkyl-1H-indole-5-urea or amide derivatives having the following formula:

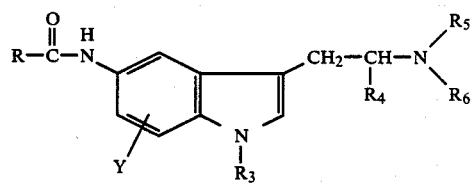

or a pharmaceutically acceptable acid addition salts thereof, wherein: R is $C_{1-4}$ loweralkyl, $C_{1-4}$ loweralkoxy, phenyl,

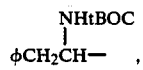

pyrrolyl, pyridyl or is a substituted nitrogen represented by:

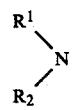

wherein $R_1$ is H or a $C_{1-4}$ loweralkyl or phenyl or cycloalkyl; $R_2$ is H or a $C_{1-4}$ loweralkyl; Y is H or halo; $R_3$ is H or a $C_{1-4}$ loweralkyl; $R_4$ is H or a $C_{1-4}$ loweralkyl; $R_5$ is H or a $C_{1-4}$ loweralkyl or carboxymethyl or carboxytrifluoromethyl; $R_6$ is H or a $C_{1-4}$ loweralkyl, and $R_5$ and $R_6$ may also be taken together as an N-loweralkyl-pyrrolidinylidene group.

11 Claims, No Drawings

3-AMINOALKYL-1H-INDOLE-5-UREA AND AMIDE DERIVATIVES

This invention relates to novel compounds which are 3-aminoalkyl-1H-indole-5-urea and 3-aminoalkyl-1H-indole-5-amide derivatives, and to their use as antihypertensive agents.

The compounds of the present invention are 3-aminoalkyl-1H-indole-5-urea and amide derivatives having the following formula I:

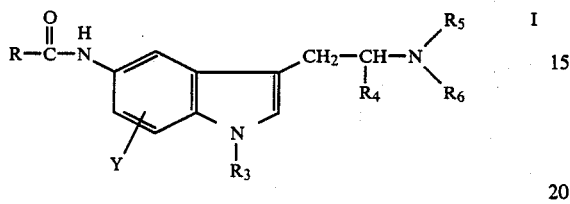

wherein: R is a $C_{1-4}$ loweralkyl, a $C_{1-4}$ loweralkyloxy, phenyl,

pyrrolyl, pyridyl or a substituted nitrogen represented by

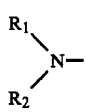

wherein: $R_1$ is H or a $C_{1-4}$ loweralkyl or phenyl or cycloalkyl and $R_2$ is H or a $C_{1-4}$ loweralkyl; Y is H or halo; $R_3$ is H or a $C_{1-4}$ loweralkyl; $R_4$ is H or a $C_{1-4}$ loweralkyl; $R_5$ is H or a $C_{1-4}$ loweralkyl or a $C_{1-4}$ loweralkylcarbonyl or trifluoromethylacetyl; $R_6$ is H or a $C_{1-4}$ loweralkyl, and $R_5$ and $R_6$ may also be taken together as an N-loweralkyl-pyrrolidinylidene group.

Thus when R is the substituted nitrogen $NR_1R_2$, the compounds are 3-aminoalkyl-1H-indole-5-urea derivatives of formula Ia:

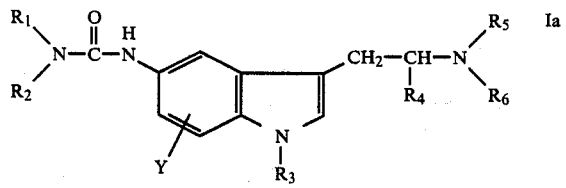

The term "halo" includes chloro, fluoro, bromo, and iodo. The $C_{1-4}$ loweralkyl may be straight chain e.g. methyl, ethyl, butyl, or branched chain, e.g., isopropyl.

The pharmaceutically acceptable acid addition salts may be obtained from a wide variety of acids, both inorganic and organic. Illustrative examples of such salts are the hydrochloride, hydrobromide, phosphate, sulfate, p-toluenesulfonate, benzenesulfonate, malonate, succinate, methosulfate, methanesulfonate, 2-napsylate and the like. The compounds of the invention, and salts thereof, may be obtained in the form of a hydrate, and these are included in the compounds claimed, even if not specifically stated.

GENERAL METHODS OF PREPARATION

The preparation of the compounds of Formula I generally involve the synthesis of an intermediate of Formulas II–V:

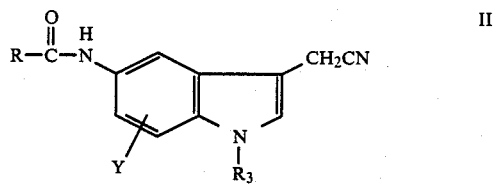

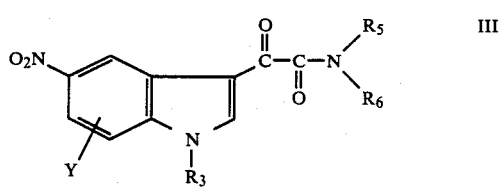

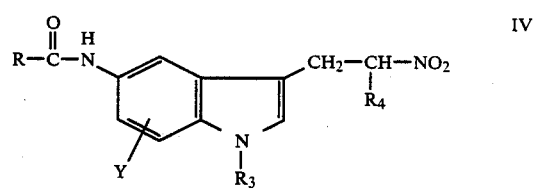

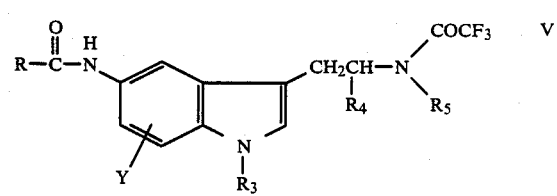

in which intermediates either a readily reducible or hydrolyzable functional chain in the 3-position of the indole would yield the substituted nitrogen substituent

The reduction of the cyanoalkyl, oxamyl or nitroalkyl functionalities of intermediates II–IV respectively can be realized by the chemical or catalytic methods well-known in the art. The chemical reductions may be accomplished with hydrides such as lithium aluminum hydride and diborane, the latter being preferred. Catalytic reductions may employ either Raney nickel or noble metal catalysts, with Raney nickel being preferred. The hydrolysis of the trifluoroacetyl functionality of intermediate V is readily accomplished under basic conditions; the use of potassium hydroxide in aqueous methanol being the procedure of choice.

To further describe the synthesis of intermediates II–V and specific compounds of this invention in a simple manner, these procedures are illustrated in Schemes A–E, with notation of appropriate working examples.

Preparation of intermediates of formula II from the appropriate 5-aminoindoleacetonitriles is outlined in Scheme A. The requisite 5-aminoindoleacetonitriles are readily available from the corresponding 5-nitroindoles through the gramine synthesis.
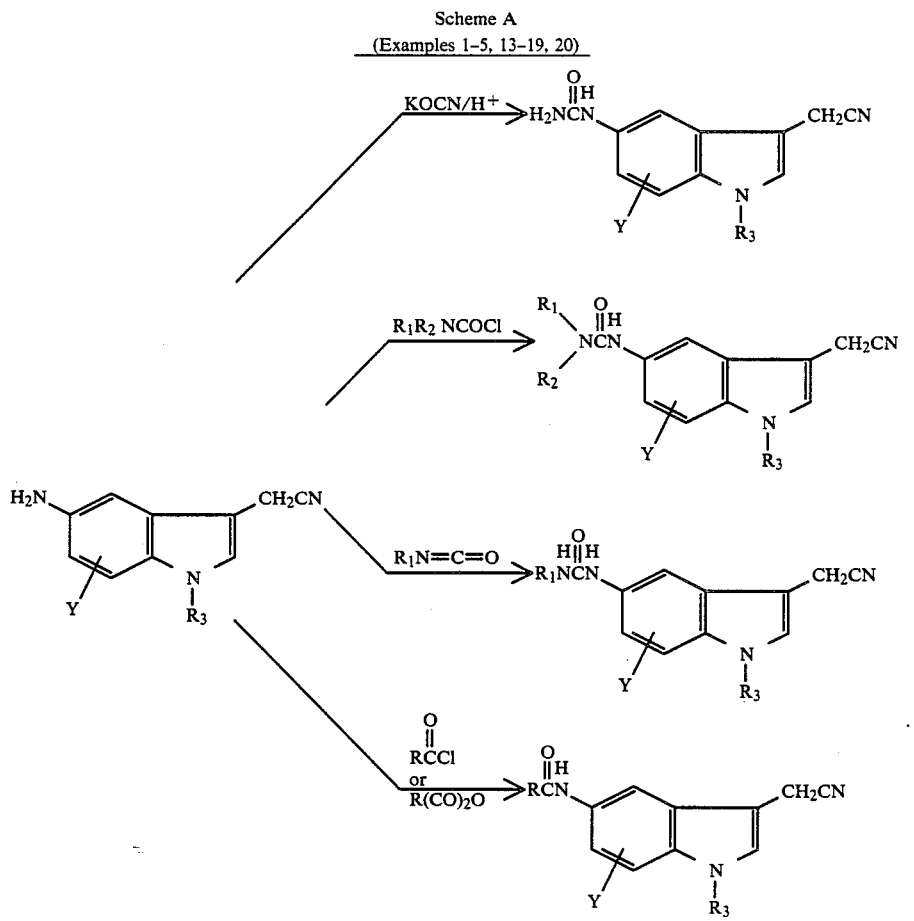
Scheme A (Examples 1-5, 13-19, 20)
Likewise the synthesis and utilization of intermediates of Formula III is illustrated in Scheme B.
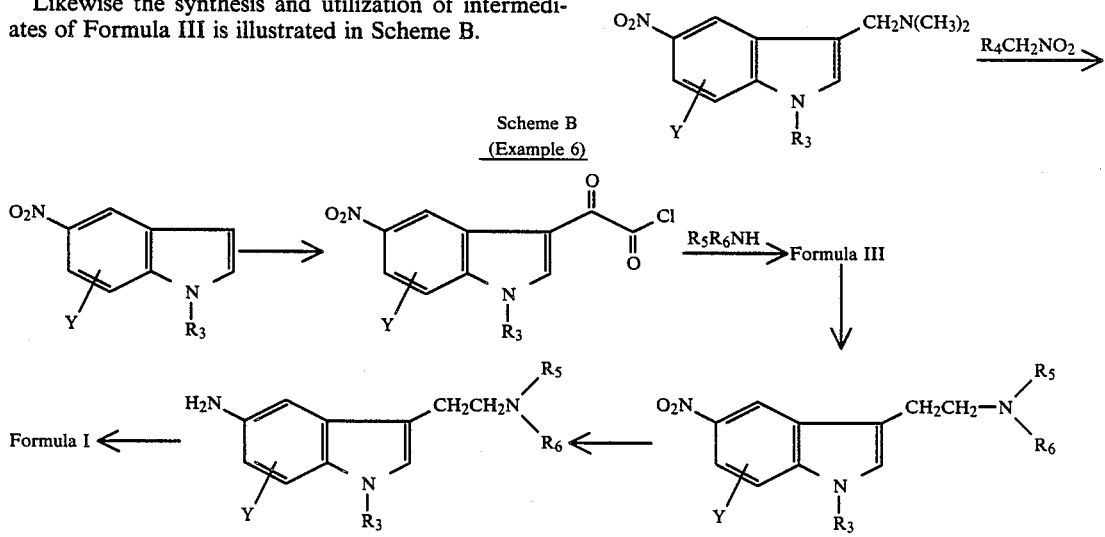
Scheme C (Example 12)
Scheme B (Example 6)
Intermediates IV are prepared from the corresponding 5-nitrogramines as illustrated in Scheme C.

-continued
Scheme C (Example 12)

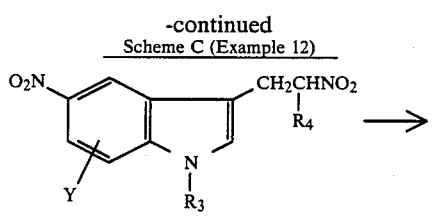

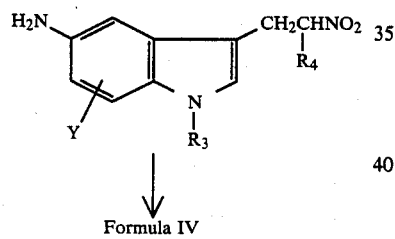

Formula IV

The synthesis of acyl intermediates of Formula V from appropriate 5-nitrotryptamines, themselves readily available by reduction, diborane being preferred, from 5-nitroindoleacetonitriles is outlined in Scheme D.

and acylative procedures of primary or secondary amines well-known in the chemical literature. Scheme E is meant to be representative of these further chemical manipulations.

Scheme E (Examples 7, 10, 11)

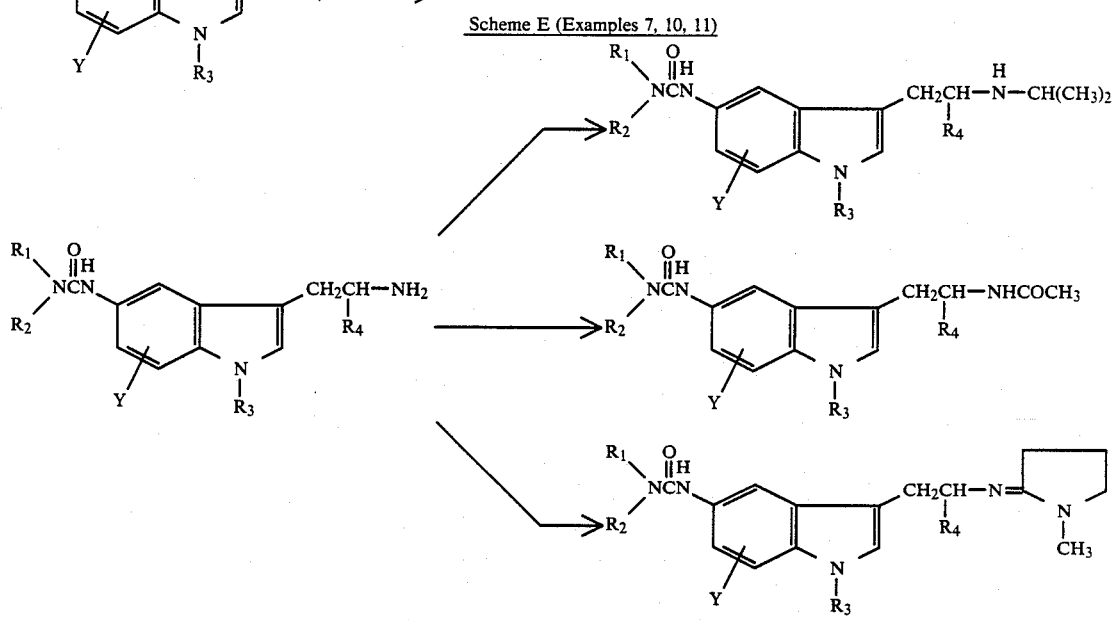

The compounds of Formula I have been found to alleviate hypertension and to be useful antihypertensive agents as determined in the antihypertensive test hereinafter described.

RODENT ANTIHYPERTENSIVE SCREEN

This test evaluates compounds for effects on arterial pressure and heart rate. In this test, the arterial pressure of adult spontaneously hypertensive rats [SHR] (Charles River) is monitored directly via an aortic cannula. The SHR rats are anesthetized with an inhalation anesthetic (methoxyflurane). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. Heart rate is determined from

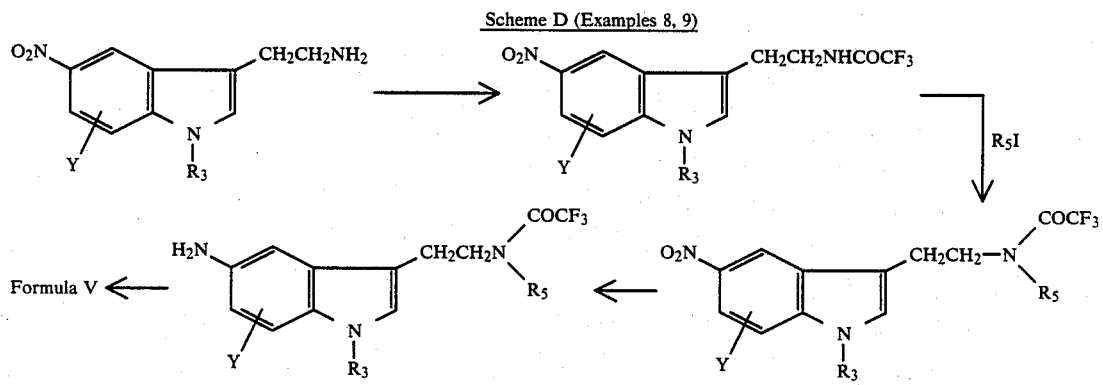

Further structural modifications of compounds of general Formula I in which at least one of $R_5$ and $R_6$ are hydrogen are readily available through those alkylative the arterial pressure recording. The test compounds are administered either orally (p.o.) by gavage or by intraperitoneal (i.p.) injection at a dose of 10-100 mg/kg.

The arterial pressure and heart rate are monitored for a minimum of 24 hours. A test compound is considered to be active as an antihypertensive agent if the mean arterial pressure (MAP) indicates a fall of >15 mm of Hg. Each animal serves as his own control.

The results of this test employing at least three (3) rats per dose level for each compound and performed with 3-aminoalkyl-1H-indole-5-urea and amide compounds of this invention are shown in Tables I and II.

The compounds were administered in the form shown in the title of the Example showing how to make the compound i.e. as the free base, hydrate, salt, etc.

Test results in Tables I and II show the usefulness of the compounds of this invention in the treatment of hypertension.

TABLE I

Antihypertensive Determination-Spontaneously Hypertensive (SH) Rat

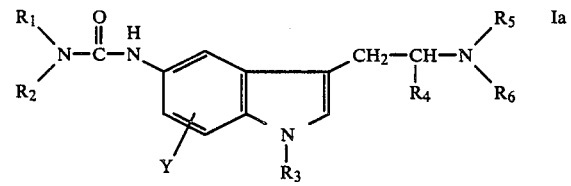

| | | | Dose mg/kg (p.o. or i.p.) | Decrease in MAP (mm Hg) | Duration (hrs.) |
|---|---|---|---|---|---|
| Formula Ia, $R_3$–$R_6$ and Y = H | | | | | |
| Ex. No. | $R_1$ | $R_2$ | | | |
| 1 | H | H | 30 p.o. | 48 | 15 |
| 2 |  | H | 100 p.o. | 36 | 4 |
| 3 | φ | H | 100 p.o. | 33 | 4 |
| 4 | $CH_3$ | H | 30 p.o. | 28 | 4.5 |
| 5 | $CH_3$ | $CH_3$ | 100 p.o. | 55 | 4 |
| Formula Ia, $R_1$–$R_4$ and Y = H | | | | | |
| Ex. No. | $R_5$ | $R_6$ | | | |
| 6 | $CH_3$ | $CH_3$ | 100 p.o. | 20 | 2 |
| 7 | $COCH_3$ | H | 30 i.p. | 28 | 2.75 |
| 8 | $COCF_3$ | $CH_3$ | 100 p.o. | 44 | 4 |
| 9 | $CH_3$ | H | 10 p.o. | 35 | 4 |
| 10 | $CH(CH_3)_2$ | H | 10 p.o. | 25 | 4 |
| 11 | 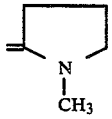 | | 25 i.p. | 30 | 1 |
| Formula Ia, $R_1$, $R_2$, $R_5$ and $R_6$ = H | | | | | |
| Ex. No. | $R_3$ | $R_4$ | Y | | |
| 12 | H | $CH_3$ | H | 30 i.p. | 35 | 1 |
| 13 | $CH_3$ | H | H | 30 i.p. | 53 | 0.5 |
| 14 | H | H | Cl | 35 p.o. | 25 | — |

TABLE II

Antihypertensive Determination - Spontaneously Hypertensive (SH) Rat

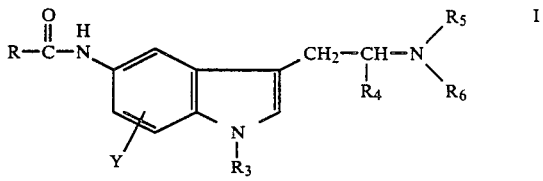

Formula I, $R_3$–$R_6$ and Y = H

| Ex. No. | R | Dose mg/kg (p.o. or i.p.) | Decrease in MAP (mm Hg) | Duration (hrs.) |
|---|---|---|---|---|
| 15 | $-CH_3$ | 20 p.o. | 50 | 4 |
| 16 |  | 10 p.o. | 60 | 4 |
| 17 | $-\phi$ | 100 p.o. | 37 | 3 |
| 18 | $-CH-CH_2\phi$<br>$\|$<br>$NH-tBoc$ | 30 p.o. | 17 | 0.5 |
| 19 | $-OCH_2CH_3$ | 100 p.o. | 33 | 2 |

The compounds of the present invention are useful for treating hypertension by administering to subjects in need of treatment an effective hypertension reducing amount of an indole of Formula I or it's pharmaceutically-acceptable salt as active agent. The active agents may or may not be administered as an admixture with a pharmaceutically-accepted carrier.

The operable range for carrying out the treatment is the administration, orally or parenterally, of from 1 milligram to 500 milligrams of said compound of Formula I. Operable amounts are generally within the range of 1 to 100 mg/kg of body weight.

The following examples are illustrative of the invention and constitute especially preferred embodiments, but are not to be construed as limiting. All temperatures are in degrees Celsius.

EXAMPLE 1

N-[3-(2-Aminoethyl)-1H-indol-5-yl]urea

5-Aminoindole-3-acetonitrile:

A suspension of 25.0 g (0.124 mole) of 5-nitroindole-3-acetonitrile[1] and 4 g of $PtO_2$ in 600 ml of EtOH was hydrogenated in a Parr apparatus for 20 hours. The catalyst was filtered and solvents removed in vacuo to give 21.3 g (100% yield) of crude 5-aminoindole-3-acetonitrile: m.p. 125°-130° (lit[2] 129-135). Dry column chromatography (EtOAc/silica gel) yields pure product in 71% yield; m.p. 142°-143°.

[1](G. Cavallini and V. Ravenna, Il Farmco Ed. Sci., 13, 105 (1958); CA 52: 20126 d.) [2](U.S. Pat. No. 3,472,860, p. 5.)

N-(3-Cyanomethyl-1H-indol-5-yl)urea:

To a solution of 21.3 g (0.124 mole) of 5-aminoindole-3-acetonitrile in 400 ml of 25% aq HOAc cooled to 0° was added 10.5 g (0.13 mole) of KOCN in 30 ml of $H_2O$. The reaction mixture was stored at 0° for 14 hours after which a beige solid was filtered and recrystallized from methanol to give 14.0 g (53% yield) of N-(3-cyanomethyl-1H-indol-5-yl)urea. Further recrystallization affords an analytical sample: m.p. 219°–220°; i.r. (Nujol) 3455, 3300, 2250 and 1650 cm$^{-1}$; nmr (d$_6$-DMSO) δ(TMS) 11.06 (1,S,indole NH ), 8.46 (1,S, —NHCO—), 7.70 (1,d,J$_{meta}$=2 Hz), 7.37 (1,d,J$_{ortho}$=9 Hz), 7.30 (1,S,indole C$_2$H), 7.18 (1,d of d,J$_{ortho}$=9 Hz, J$_{meta}$=2 Hz), 5.73 (2,S,—CONH$_2$) and 4.00 ppm (2,S,—CH$_2$CN).

Anal. Calcd for C$_{11}$H$_{10}$N$_4$O: C, 61.67; H, 4.71; N, 26.16. Found: C, 61.82; H, 4.94; N, 26.27.

N-[3-(2-Aminoethyl)-1H-indol-5-yl]urea:

A suspension of 11.0 g (0.05 mole) of N-(3-cyanomethyl-1H-indol-5-yl)urea in 700 ml of abs. EtOH saturated with NH$_3$ was treated with RaNi (one spoonful, activated by washing with 1 l of abs EtOH) and hydrogenated in a Parr apparatus for 14 hours. The solution was filtered through celite and then through a millipore followed by evaporation of solvents in vacuo to give an oily solid. Trituration with EtOH afforded 8.2 g of crude white product: m.p. 187.5°–188.5°. Thin layer chromatography indicated an approximately 5% impurity (3% NH$_4$OH - MeOH/silica gel). Dry column chromatography (1.5 g/400 g of silica gel—3% NH$_4$OH/MeOH elluent) affords 4.8 g of pure N-[3-(2-aminoethyl)-1H-indol-5-yl]urea: m.p. 188.5°–189.5°; i.r. (KBr) 3400, 3360, 3280, 3200, and 1650 cm$^{-1}$; nmr (d$_6$-DMSO) δ(TMS) 10.72 (1,S,indole NH), 8.37 (1,S,—NHCO—), 7.65 (1,d, J$_{meta}$=2 Hz), 7.27 (1,d,J$_{ortho}$=8 Hz), 7.10 (1,S,indole C$_2$H), 7.02 (1,d of d, J$_{ortho}$=8 Hz, J$_{meta}$=2 Hz), 5.71 (2,S,—CONH$_2$), 2.78 (4,S,—CH$_2$CH$_2$—) and 2.30 ppm (2,S,—NH$_2$).

Anal. Calcd for C$_{11}$H$_{14}$N$_4$O: C, 60.53; H, 6.47; N, 25.67. Found: C, 60.48; H, 6.48; N, 25.65.

EXAMPLE 2

N-[3-(2-Aminoethyl)-1H-indol-5-yl]-N'-cyclohexylurea Hydrate (4:1)

N-(3-Cyanomethyl-1H-indol-5-yl)-N'-cyclohexylurea

To a solution of 7.0 g (0.041 mole) of 5-aminoindole-3-acetonitrile in 100 ml of abs ethanol, at 0° under nitrogen atmosphere, was added 5.23 ml (0.041 mole) of cyclohexylisocyanate dropwise. After stirring at 0° for one hour the product was filtered and recrystallized from ethanol to give 6.78 g (56% yield) of desired product: m.p. 233°–234°; i.r. (Nujol) 3300, 3275, 2245 and 1622 cm$^{-1}$.

N-[3-(2-Aminoethyl)-1H-indol-5-yl]-N'-cyclohexylurea:

A suspension of 6.68 g (0.023 mole) of the nitrile above was reduced as in Example 1 with RaNi. The resultant beige solid was recrystallized from methanol to afford 2.95 g (43% yield) of pure product: m.p. 169°–171°; i.r. (KBr) 3350, 3290, 1640 and 1560 cm$^{-1}$; nmr (d$_6$-DMSO) δ(TMS) 10.52 (1, S, indole—NH), 8.06 (1, S, In—NHCO—), 7.61 (1, d, J$_{4-6}$=2 Hz, H-4), 7.20 (1, d, J$_{6-7}$=8 Hz, H-7), 7.04 (1, S, H-2), 6.95 (1, d of d, J$_{6-7}$=8H,J$_{4-6}$=2 Hz, H-6), 5.94 (1, d, J=8 Hz, CH—NHCO—), 3.45 (1, broad S,

), 2.75 (4, S, —CH$_2$—CH$_2$), and 1.2–1.8 ppm (10, m, cyclohexyl).

Anal. Calcd for C$_{17}$H$_{24}$N$_4$O.¼H$_2$O: C, 66.96; H, 8.10; N, 18.38; H$_2$O, 1.48. Found: C, 66.56; H, 8.08; N, 18.23; H$_2$O, 1.25.

EXAMPLE 3

N-[3-(2-Aminoethyl)-1H-indol-5-yl]-N'-phenylurea Hydrate (5:1)

N-(3-Cyanomethyl-1H-indol-5-yl)-N'-phenylurea:

The method of Example 2 was applied to phenylisocyanate (3.18 ml, 0.029 mole) to give after recrystallization from ethanol, 4.69 g (56% yield) of product: m.p. 217°–219°; i.r. (nujol) 3300, 3275, 2230 and 1620 cm$^{-1}$.

N-[3-(2-Aminoethyl)-1H-indol-5-yl]-N'-phenylurea:

A suspension of 4.59 g (0.016 mole) of the nitrile above was reduced as in Example 1 with RaNi to give 4.1 g of crude product. The crude product was purified via dry column chromatography (3% NH$_4$OH in methanol/silica gel) followed by recrystallization from methanol to give pure desired product (1.1 g, 24% yield): m.p. 192°–194° ; i.r. (KBr) 3325, 1645, 1600 and 1560 cm$^{-1}$; nmr (d$_6$-DMSO) δ(TMS) 10.60 (1, S, indole NH), 8.58 (1, S, Ar—NHCO—), 8.42 (1,S, Ar—NHCO), 7.70 (1, d, J$_{4-6}$=2 H$_z$, H-4), 6.85–7.55 (8, m, indole and phenyl) and 2.75 ppm (4, S, —CH$_2$CH$_2$—).

Anal. Calcd for C$_{17}$H$_{18}$N$_4$O.1/5 H$_2$O: C, 68.52; H, 6.22; N, 18.80; H$_2$O, 1.21. Found: C, 68.73; H, 6.31, N, 18.90; H$_2$O, 1.10.

EXAMPLE 4

N-[3-(2-Aminoethyl)-1H-indol-5-yl]-N'-methylurea 2-Naphthalenesulfonate Hydrate (16:16:1)

N-[3-(Cyanomethyl)-1H-indol-5-yl]-N'-methylurea:

The method of Example 2 was applied to methyl isocyanate (2.5 ml, 0.042 mole) to give a precipitate which was filtered, washed with cold EtOH and dried to yield 7.3 g of grey solid: m.p. 205°–215° (dec.). It was used for the next reaction without purification.

N-[3-(2-Aminoethyl)-1H-indol-5-yl]-N'-methylurea:

A suspension of 4.5 g (0.02 mole) of N-[3-(cyanomethyl)-1H-indol-5-yl]-N'-methylurea was reduced as in Example 1 with RaNi to give 4.5 g of crude product. It was taken up in 100 ml of isopropyl/alcohol and 4.0 g (0.02 mole) of 2-naphthalene sulfonic acid was added. The oily ppt solidified on continued trituration. It was filtered, washed with a small amount of isopropyl alcohol and dried. It was recrystallized twice from ethanol giving 3.40 g; m.p. 188°–190°.

Anal. Calcd for C$_{12}$H$_{16}$N$_4$O.C$_{10}$H$_8$SO$_3$.1/16 H$_2$O: C, 59.83; H, 5.48; N, 12.68; H$_2$O, 0.26. Found: C, 59.91; H, 5.56; N, 13.14; H$_2$O, 0.66.

EXAMPLE 5

N-[3-(2-Aminoethyl)-1H-indol-5-yl]-N',N'-dimethylurea (4-Methylphenyl)sulfonate (1:1)

N-[3-(Cyanomethyl)-1H-indol-5-yl]-N',N'-dimethyurea:

To a solution of 7.0 g (0.041 mole) of 5-aminoindole-3-acetonitrile and 5.7 ml (0.041 mole) of Et$_3$N in 100 ml of abs EtOH, under N$_2$, was added 3.78 ml of dimethylcarbamyl chloride (0.041 mole). The reaction was stirred at room temperature for 24 hours. The solvent was removed in vacuo to yield a black goo (7.5 g). It was purified by dry column chromatography. Eluting it with ethylacetate first and then with 5% MeOH in EtOAc to give 3.5 g of brown solid. It was charcoaled to remove the color (MeOH as solvent). Removal of solvent gave 1.4 g of white product.

N-[3-(2-Aminoethyl)-1H-indol-5-yl]-N',N'-dimethylurea:

1.40 g (0.006 mole) of the nitrile above, was reduced as in Example 1 with RaNi giving a white solid (1.30 g) m.p. 157°–160°. To 0.67 g (0.003 mole) of the free base was added 0.49 g (0.003 mole) of p-toluene-sulfonic acid hydrate in 26 ml of isopropyl alcohol. The ppt salt was collected on a filter, washed with cold isopropyl alcohol and ether, and dried giving 0.75 g of the tosylate salt. Recrystallization three times from ethanol-ether gave 0.45 g of product: m.p. 187°–189°.

Anal. Calcd for $C_{13}H_{18}N_4O \cdot C_7H_8O_3S$: C, 57.40; H, 6.26; S, 7.65; N, 13.39. Found: C, 57.12; H, 6.43; N, 13.29.

EXAMPLE 6

N-[3-(2-Dimethylaminoethyl)-1H-indol-5-yl]urea (E)-2-Butenedioate (2:3) Hydrate (10:1)

N,N-Dimethyl-5-nitroindole-3-oxalylamide:

A suspension of 16.5 g (0.065 mole) of 5-nitroindole-3-oxalyl chloride in 250 ml of dry THF under nitrogen was treated with 18 g of Me$_2$NH dissolved in 170 ml of THF dropwise at a rate to maintain 35°. After stirring 24 hours at room temperature, the suspension was filtered and the filtrate evaporated in vacuo to give a yellow solid. Trituration with water gave 11.2 g (66% yield) of the desired oxalylamide; m.p. 239°–241°.

N,N-Dimethyl-5-nitrotryptamine:

A suspension of 7.95 g (0.03 mole) of the oxalylamide, above, in 275 ml of dry THF was treated with 61 ml (0.06 mole) of 1M B$_2$H$_6$ in THF. After 3 hours, the excess diborane was quenched with 1N HCl and solvents removed in vacuo. The resultant orange solid was dissolved in 250 ml of hot 20% HCl, filtered and cooled. The precipitated product was filtered and dried to give 4.9 g (60% yield) of the tryptamine: nmr (d$_6$-DMSO) δ(TMS) 8.72 (1, d, $J_{4-6}=2$ Hz, H-4), 8.10 (1, d of d, $J_{6-7}=8$ Hz, $J_{4-6}=2$ Hz, H-6), 7.60 (1, d, $J_{6-7}=8$ Hz, H-7), 7.55 (1, S, H-2), 3.32 (4, S, —CH$_2$CH$_2$—), 2.97 (3, S, N—CH$_3$) and 2.86 (3, S, NCH$_3$); mass spectrum (70 e/v) m/e 233.

N-[3-(2-Dimethylaminoethyl)-1H-indol-5-yl] urea:

A suspension of 4.7 g (0.017 mole) of the nitrotryptamine above in 150 ml of THF was neutralized to pH ~7.5–8.0 with NH$_4$OH to effect solution. The solution was treated with 1.0 g 10% Pd-C and hydrogenated in a Parr apparatus for ½ hour. The catalyst was filtered and solvents evaporated in vacuo to give a light brown oil, the 5-amino-N,N-dimethyltryptamine. The brown oil was dissolved in 100 ml of methanol and treated with 3 ml of con.HCl followed by 2.8 g (0.035 mole) of KNCO. Additional HCl and KNCO was added until the reaction was complete. The reaction mixture was filtered and solvent removed in vacuo to give a red oil. The red oil was purified via dry column chromatography (2% NH$_4$OH in MeOH, silica gel). The resultant 2.69 g of oil was dissolved in 80 ml of methanol and treated with 1.23 g (0.01 mole) of fumaric acid. On sitting, the fumarate precipitated. The precipitate was filtered and recrystallized from EtOH/H$_2$O to afford 2.1 g (30% overall yield) of the desired urea: m.p. 199°–200° (dec); i.r. (KBr) 3420, 3350, 2450, and 1650 cm$^{-1}$; nmr (d$_6$-DMSO) δ(TMS) 10.68 (1, S, indole —NH), 9.75 (1, broad S, —N$^⊕$H), 8.38 (1, S, —NHCO—), 7.58 (1,d, $J_{4-6}=2$ Hz, H-4.), 7.21 (1, d, $J_{6-7}=8$ Hz, H-7), 7.10 (1, S, H-2), 7.05 (1, d of d, $J_{6-7}=8$ Hz, $J_{4-6}=2$ Hz, H-6), 6.56 (3, S, =CH—CO$_2$H), 5.70 (2, broad S, —CONH$_2$), 3.05 (4, broad S, —CH$_2$CH$_2$—) and 2.69 ppm (6, S, N-dimethyl).

Anal. Calcd for $C_{13}H_{18}N_4O \cdot 1.5\ C_4H_4O_4 \cdot 1/10\ H_2O$: C, 54.05; H, 5.78; N, 13.27; H$_2$O, 0.43. Found: C, 54.31; H, 5.83; N, 13.44; H$_2$O, 0.48.

EXAMPLE 7

N-[2-5-[(Aminocarbonyl)amino]-1H-indol-3-yl}ethyl}acetamide with Ethanol (10:1)

A suspension of 3.0 g (0.014 mole) of N-[3-(2-aminoethyl)-1H-indol-5-yl]urea, Example 1, in 25 ml of pyridine was treated with 10 ml of acetic anhydride. Within ½ hour a clear solution formed followed immediately by precipitation of desired product. The off-white solid was filtered, washed with water and air-dried. Recrystallization from ethanol afforded 1.90 g (51%) of pure product: m.p. 220°–221°; i.r. (KBr) 3420, 3315, 1640, 1610 and 1535 cm$^{-1}$; nmr (d$_6$-DMSO) δ(TMS) 10.53 (1, S, indole-NH), 8.18 (1, S, —NHCO—), 7.84 (1, t, —CH$_2$NHCO), 75.2 (1, d, $J=2$ Hz, H-4), 7.17 (1, d, $J_{7-6}=9$ Hz, H-7), 7.06 (1, S, H-2), 7.00 (1, d of d, $J_{6-7}=9$ Hz, $J_{6-4}=2$ Hz, H-6), 5.60 (2, S, —CONH$_2$), 3.28 (2, M, —CH$_2$—NHCO), 2.72 (2, M, indole—CH$_2$) and 1.78 ppm (3, S, —COCH$_3$).

Anal. Calcd for $C_{13}H_{16}N_4O_2 \cdot 1/10\ C_2H_6O$: C, 59.85; H, 6.32; N, 21.15. Found: C, 59.78; H, 6.40; N, 21.17.

EXAMPLE 8

N-{2-{5-[(Aminocarbonyl)amino]-1H-indol-3-yl}ethyl}-N-methyl-2,2,2-trifluoroacetamide N-(5-Nitro-1H-indol-3-yl)ethyl-2,2,2-trifluoroacetamide:

To a suspension of 24.09 g (0.118 mole) of 5-nitrotryptamine in 600 ml of dry methylene chloride was added 36.1 g (0.172 mole) of trifluoroacetic anhydride in 50 ml of dry CH$_2$Cl$_2$. The reation was stirred at RT 2 hours and then concentrated in vacuo to give a yellow-brown solid which on recrystallization from 500 ml of EtOH afforded 23.68 g (67% yield) of desired product: m.p. 197–199. An analytical sample was obtained via recrystallization from CH$_2$Cl$_2$/EtOH: m.p. 199.5°–201° ; nmr (d$_6$-DMSO) δ(TMS) 11.63 (1, S, indole—NH), 9.50 (1, broad S, —NHCOCF$_3$), 8.60 (1, d, $J_{4-6}=2$Hz, H-4), 8.03 (1, d of d, $J_{4-6}=2$Hz, $J_{6-7}=8$Hz, H-6), 7.55 (1, d, $J_{6-7}=8$Hz, H-7), 7.41 (1, S, H-2), 3.50 (2, M, —CH$_2$—) and 3.02 ppm (2, M, —CH$_2$—); CI-MS, m/e 301. Anal. Calcd. for $C_{12}H_{10}F_3N_3O_3$: C, 47.84; H, 3.35; N, 13.95. Found: C, 47.88; H, 3.35; N, 13.83.

N-(1-Benzyloxycarbonyl-5-nitro-1H-indol-3-yl)ethyl-2,2,2-trifluoroacetamide:

A solution of 15.0 g (0.05 mole) of amide above in 300 ml of dry acetone was treated with 5.73 ml (0.051 mole) of benzyl chloroformate followed by 3.4 g (0.052 mole) of powdered 86% KOH. After 2 hours an additional 2 ml of benzyl chloroformate and 0.2 g of KOH were added. After another hour the solvent was removed in vacuo and the residue triturated with ether to give 18.8 g of a white solid: m.p. 190°. Recrystallization from ethanol afforded desired product in 72% yield: m.p. 189°–190°; nmr (d$_6$-DMSO) δ(TMS) 9.56 (1, broad S, —NHCOCF$_3$), 8.66 (1, S, H-4), 8.30 (2, S, H-6, 7), 7.82 (1, S, H-2), 7.50 (5, m, —φ), 5.54 (2S, —CH$_2$—φ), 3.50 (2, m, —CH$_2$—) and 3.00 ppm (2, m, —CH$_2$—).

Anal. Calcd for $C_{20}H_{16}F_3N_3O_5$: C, 55.17; H, 3.70; N, 9.65. Found: C, 55.15; H, 3.89; N, 9.54.

N-(1-Benzyloxycarbonyl-5-nitro-1H-indol-3-yl)ethyl-N-methyl-2,2,2-trifluoroacetamide:

A suspension of 18.8 g of the crude protected indole (above) in 500 ml of dry acetone was treated with 10.7 ml (0.17 mole) of $CH_3I$ followed by 2.52 g (0.045 mole) of powdered 86% KOH. After stirring 3 hours the solvent was removed in vacuo and the residue dissolved in 400 ml $CH_2Cl_2$, filtered, charcoaled and evaporated in vacuo to give a gold oil which solidified on standing. Recrystallization from EtOH afforded 13.2 g of pure product: m.p. 107°–109°; nmr ($d_6$-DMSO) $\delta$(TMS) 8.68 (1, S, H-4), 8.30 (2, S, H-6,7), 7.82 (1, m, H-2), 7.52 (5, m, $\phi$), 5.51 (2, S, —$CH_2\phi$), 3.71 (2, m, —$CH_2$—), and 3.15 ppm (5, m, —N—$CH_2$— and N—$CH_3$).

Anal. Calcd for $C_{21}H_{18}F_3N_3O_5X$: C, 56.13; H, 4.04; N, 9.35. Found: C, 56.18; H, 4.07; N, 9.37.

N-[2-(5-Aminoindol-3-yl)ethyl]-N-methyl-2,2,2-trifluoroacetamide (E)-2-Butenedioate (1:1)

A solution of 1.56 g (0.0035 mole) of the product above in 50 ml of THF was treated with 2 g of 10% Pd/C and hydrogenated in a Parr apparatus at 50 psi for 3 hours. The spent catalyst was filtered and the filtrate removed in vacuo to leave 1.0 g of a gold oil. The oil was dissolved in 20 ml of EtOH and treated with 18 ml of a 0.2M solution of fumaric acid in EtOH. The precipitated salt was filtered and again recrystallized from EtOH to give 0.82 g (58% yield) of product: m.p. 195°–196.5°; ir (KBr) 3330, 2930, 2620, and 1695 cm$^{-1}$; nmr ($d_6$-DMSO) $\delta$(TMS) 10.41 (1, S, indole —NH), 8.12 (4, S, NH, exchangeable), 7.08 (1, d, $J_{6-7}=8H_z$, H-7), 7.00 (1, d, J=1.5H$_z$, H-2), 6.79 (1, pair of d in 60/40 ratio, $J_{4-6}=2H_z$, H-4, exchangeable with heat and acid), 6.61 (2, S, fumarate), 6.55 (1, d, $J_{4-6}=2H_z$, $J_{6-7}=8H_z$, H-6), 3.62 (2, M, —$CH_2$—), 3.05 (3, pair of S in 40/60 ratio, N—$CH_3$) and 2.88 ppm (2, pair of m, —$CH_2$—N—).

Anal Calcd for $C_{13}H_{14}F_3N_3O \cdot C_4H_4O_4$: C, 50.87; H, 4.52; N, 10.47. Found: C, 50.86; H, 4.57; N, 10.65.

N-{2-{5-[(Aminocarbonyl)amino]-1H-indol-3-yl}ethyl}N-methyl-2,2,2-trifluoroacetamide To a solution of 7.2 g (0.025 mole) of the aminoindole above in 400 ml of MeOH was added 4.08 g (0.05 mole) of KNCO followed by 4.4 ml con HCl. After two hours the reaction mixture was filtered and the filtrate decolorized with charcoal and concentrated in vacuo to give a beige solid. The solid was triturated with EtOAc/$H_2O$ (7:2) and then recrystallized from methanol to give 5.64 g (69%) of desired product: m.p. 193°–194.5° ; i.r. (KBr) 3440, 3340, and 1675 cm$^{-1}$; nmr ($d_6$-DMSO) $\delta$(TMS) 10.60 (1, S, indole—NH), 8.19 (1, S, —NH-CO—), 7.55 (1, S, H-4), 7.21 (1, d, $J_{6-7}=8H_z$, H-7), 7.12 (1, S, H-2), 7.05 (1, d of d, $J_{6-7}=8H_z$, $J_{4-6}=1.5$ Hz, H-6), 5.62 (2, S, —$CONH_2$), 3.63 (2, m, indole —$CH_2$—), 3.04 (3, S, —$CH_3$) and 2.90 ppm (2, M, $CH_2$—N<).

Anal. Calcd for $C_{14}H_{15}F_3N_4O_2$: C, 51.22; H, 4.61; N, 17.07. Found: C, 51.30; H, 4.68; N, 17.15.

EXAMPLE 9

N-[3-(2-Methylaminoethyl)-1H-indol-5-yl]urea Hydrate (6:1), compound with acetone (10:1)

A suspension of 4.33 g (0.014 mole) of the trifluoroacetamide compound, Example 8, in 100 ml of $H_2O$ was treated with 50 ml of a 5% KOH in MeOH solution. This mixture as heated at reflux for $\frac{1}{2}$ hour, cooled and neutralized to pH=7.2 with 1N HCl. The solvents were removed in vacuo and the resultant oil purified by column chromatography (0.75% $NH_4OH$/MeOH on silica gel). The purified oil was triturated with acetone repeatedly to give desired product as a white solid: m.p. 158.5°–160°.

Anal. Calcd for $C_{12}H_{16}N_4O \cdot 1/6$ $H_2O \cdot 1/10$ $C_3H_6O$: C, 61.28; H, 7.08; N, 23.24; $H_2O$, 1.25. Found: C, 61.05; H, 6.93; N, 23.08; $H_2O$, 0.97.

EXAMPLE 10

N-[3-(2-Methylethylaminoethyl)-1H-indol-5-yl]urea

A solution of 3.0 g (0.014 mole) of N-[3-(2-aminoethyl)-1H-indol-5-yl]urea, Example 1, in 100 ml MeOH was treated with 1.11 ml of acetone followed by 1.32 g (0.021 mole) of $NaBH_3CN$ and stirred for 18 hours. The solvent was removed in vacuo and the residue carefully dissolved in 20 ml of 20% HCl, heated for 15 minutes, cooled and neutralized with 4N NaOH to pH=12. The precipitated oil was extracted into EtOAc, dried over $MgSO_4$, filtered and evaporated to give a glassy white solid. This material was purified by column chromatography (0.75% $NH_4OH$/MeOH on silica gel) followed by recrystallization from acetone to give desired product: m.p. 145.5°–147°.

Anal. Calcd for $C_{14}H_{20}N_4O$: C, 64.59; H, 7.74; N, 21.52. Found: C, 64.41; H, 7.66; N, 21.33.

EXAMPLE 11

N-{3-{2[N-(1-Methyl-2-pyrrolidinylidene)]ethylamine}-1H-indol-5-yl]urea (E)-2-Butenedioate (1:2) Hydrate (1:0.5)

To 15.9 g (0.11 mole) of $BF_3 \cdot Et_2O$ in 20 ml ether under $N_2$ was added 7.16 g (0.084 mole) of epichlorohydrin in 20 ml ether. After stirring 2 hours, the ether was decanted and the resultant solid washed with three portions of ether, and dried under $N_2$. To this solid was added 20 ml $CH_2Cl_2$ followed by 8.32 g (0.084 mole) of N-methylpyrrolidinone in 20 ml $CH_2Cl_2$ and the mixture stirred three hours. To this Meerwein reagent was added 5.0 g (0.023 mole) of N-[3-(2-Aminoethyl)-1H-indol-5-yl]urea, Example 1, in 250 ml $CH_2Cl_2$ and stirred for 100 hrs. The solvent was decanted from the heterogenous mixture and the precipitated product treated with 100 ml 3N NaOH and stirred 18 hours. The aqueous solvent was decanted and resultant gooy solid washed with additional water. The crude product was purified by column chromatography (methanol on alumina) to give 2.6 g of product. The partially purified product was dissolved in EtOH and treated with a 0.2m solution of fumaric acid in EtOH. A small amount of impurity precipitated and was filtered. The filtrate was concentrated in vacuo and resultant white solid recrystallized twice from $H_2O$ to give pure desired product: m.p. 182°–185°.

Anal. Calcd for $C_{16}H_{21}N_5O \cdot 2C_4H_4O_4 \cdot \frac{1}{2}$ $H_2O$: C, 53.33; H, 5.59; N, 12.96; $H_2O$, 1.67. Found: C, 53.45; H, 5.56; N, 12.58; $H_2O$, 1.51.

EXAMPLE 12

N-[3-(2-Aminopropyl)-1H-indol-5-yl]urea (E)-2-Butenedioate (2:1) Hydrate (10:1)

5-Nitro-3-(2-nitropropyl)indole:

To a solution of 0.3 g (0.013 mole) of Na in 65 ml of abs EtOH was added 2.93 g (0.039 mole) of nitroethane dropwise. To the white suspension was added 2.19 g (0.01 mole) of 5-nitrogramine suspended in 40 ml of abs EtOH, followed by 2.5 g (0.02 mole) of dimethylsulfate in 20 ml of abs EtOH dropwise over 15 minutes. The mixture was stirred for 2 hours, then poured into 350 ml of ice water. The yellow solid was filtered, washed with ice water and air-dried to give 1.63 g (64%) of product: m.p. 130–131.5.

Anal. Calcd for $C_{11}H_{11}N_3O_4$:C, 53.01; H, 4.45; N, 16.86. Found: C, 53.06; H, 4.55; N, 16.66.

5-Amino-3-(2-nitropropyl)indole:

A solution of 1.5 g (0.006 mole) of 5-nitro-3-(2-nitropropyl)indole in 150 ml of EtOH treated with 100 mg of $PtO_2$ was hydrogenated (Parr) for 15 minutes. The catalyst was filtered and solvent removed in vacuo to give a yellow product which solidified on standing. Recrystallization from EtOH afforded 0.9 g (70%) of desired product: m.p. 120°–121.5°.

Anal. Calcd for $C_{11}H_{13}N_3O_2$: C, 60.26; H, 5.98; N, 19.15. Found: C, 60.42; H, 6.00; N, 19.20.

N-[3-(2-Nitropropyl)-indol-1H-5-yl]urea:

To a solution of 5.66 g (0.026 mole) of 5-amino-3-(2-nitropropyl)indole in 80 ml of 25% HOAc in $H_2O$ at 0° was added 2.27 g (0.028 mole) of KOCN dissolved in 15 ml of $H_2O$ dropwise. The solution was decanted from the resultant brown goo, which was purified by dry column chromatography (EtOAC/silica gel). The third fraction collected was concentrated and cooled to afford solid ppt which was used without further purification.

N-[3-(2-Aminopropyl)-indol-1H-5-yl]urea (E)-2-Butenedioate (2:1) Hydrate (10:1):

A solution of 3.8 g (0.015 mole) of N-[3-(2-nitropropyl)-1H-indol-5-yl]urea in 200 ml of abs EtOH saturated with $NH_3$ was treated with one spoonful of activated RaNi and hydrogenated for 2 hours. The catalyst was removed by filtration and solvents removed in vacuo to give a beige solid; 2.6 g (79% crude yield). This crude product was purified by dry column chromatography (3% $NH_4OH$-MeOH/silica gel) to give 2.0 g of product, which was dissolved in 190 ml of i-PrOH and treated with 0.94 g of fumaric acid in i-PrOH. The immediate precipitate was filtered and solvent removed in vacuo to give a goo which on heating with minimal i-PrOH affords a white precipitate. Filtration and recrystallization twice from $H_2O$ affords 0.51 g of pure desired product: m p. 236°–238°; i.r. (KBr) 3375, 3160, 1650–1700 (broad), and 1520 cm$^{-1}$; nmr (d$_6$-DMSO) δ(TMS) 10.72 (1, S, indole—NH), 8.66 (1, S, —NH-CO—), 7.51 (1, S), 7.21 (1, d, $J_{ortho}$=8 H$_z$), 7.19 (1, S, indole C$_2$-H), 7.13 (1, d of d, $J_{ortho}$=8 H$_z$, $J_{meta}$=2 H$_z$, 6.48 (1, S, =CHCO$_2$H), 5.81 (2, S, NH$_2$CO—), 5.54 (broad S, —NH$_3$), 3.3 (1, m), 2.85 (2, m, d of d) and 1.08 ppm (3, d, J=7 H$_z$).

Anal. Calcd for $C_{12}H_{16}N_4O.\frac{1}{2} H_2O$: C, 57.56; H, 6.29; N, 19.18; H$_2$O, 0.62. Found: C, 57.69; H, 6.35; N, 19.06; H$_2$O, 0.84.

EXAMPLE 13

N-[3-(2-Aminoethyl)-1-methyl-1H-indol-5-yl]urea E-2-Butenedioate (1:1) Hydrate (1:1)

1-Methyl-5-nitroindole-3-acetonitrile:

To a suspension of 11.5 g (0.057 mole) of 5-nitroindole-3-acetonitrile and 1.46 g (0.006 mole) of benzyltriethyl ammonium chloride in 120 ml of 50% (aq.) NaOH, stirred at 0°, was added, dropwise over 1.5 hours, a solution of 8.26 g (0.058 mole) of CH$_3$I in 80 ml of CH$_2$Cl$_2$. The temperature was raised to 25° and the stirring continued for 2 hours. The suspension was then poured into 800 ml of H$_2$O and filtered. The CH$_2$Cl$_2$ layer of the filtrate was taken to dryness in vacuo and the resulting yellow solid combined with the solid from the filtration. The combined solids were washed with H$_2$O, dried and recrystallized from n-BuOH to give 9.35 g (76%) of a yellow solid: m.p. 165°–166°; nmr (d$_6$-DMSO) δ(TMS) 8.54 (1, d, J=2.5 H$_z$), 8.16 (1, d of d, $J_{ortho}$=9 H$_z$, $J_{meta}$=2.5 H$_z$), 7.37 (1, d, J=9 H$_z$), 7.29 (1, S), and 3.86 ppm (5, S, N—CH$_3$ and —CH$_2$—CN).

1-Methyl-5-aminoindole-3-acetonitrile:

To a solution of 8.9 g (0.041 mole) of 1-methyl-5-nitroindole-3-acetonitrile in 600 ml of THF was added 3 g of 10% Pd/C. The mixture was hydrogenated in a Parr apparatus at 50 psi for 6 hours. The resulting mixture was filtered through celite treated with charcoal and filtered again through celite. The solvent was removed in vacuo leaving 7.2 g of the tan solid. This material was used directly without purification for the next step.

N-[3-Cyanomethyl-1-methyl-1H-indol-5-yl]urea:

A solution of 7.0 g (0.038 mole) of 1-methyl-5-aminoindole-3-acetonitrile was treated with KOCN as in Example 1 to give a beige solid which was filtered off, washed with cold water and triturated with 50% aq. EtOH to give 6.95 g (80%) of a beige solid: m.p. 250° (dec); nmr (d$_6$-DMSO) δ(TMS) 8.41 (1, s), 7.65 (1, s), 7.42–7.08 (3, m), 5.73 (2, s, —NH$_2$—), 4.00 (2, s, —CH$_2$—) and 3.73 ppm (3H, S, N—CH$_3$).

N-[3-(2-Aminoethyl)-1-methyl-1H-indol-5-yl]urea:

A suspension of 6.9 g (0.030 mole) of N-[3-cyanomethyl-1-methyl-1H-indol-5-yl urea was reduced with RaNi as in Example 1 to give an oily residue (~6.0 g). It was purified by dry column chromatography (alumina) with 3% NH$_4$OH in MeOH. The first fraction was a major impurity. The second fraction gave 3.01 g of oily product. It was taken up in a minimum amount of ethanol (with warming) and 1.50 g of fumaric acid was added and cooled. The ppt solid was filtered and dried. It was recrystallized from water/EtOH to give a yellowish solid (1.62 g): m.p. 180°–182°.

Anal. Calcd for $C_{12}H_{16}N_4O.C_4H_4O_4.14/15 H_2O$: C, 52.69; H, 5.99; N, 15.36; H$_2$O, 4.60. Found: C, 52.99; H, 6.03; N, 15.47; H$_2$O, 4.53.

EXAMPLE 14

N-[3-(2-Aminoethyl)-6-chloro-1Hindol-5-yl]urea 4-(Methylphenyl)sulfonate (1:1)

5-Amino-6-chloroindole-3-acetonitrile:

This intermediate was prepared by the sequence 6-chloroisatin, 6-chloro-5-nitroisatin, 6-chloro-5-nitroindole, 6-chloro-5-nitrogramine and 6-chloro-5-nitroindole-3-acetonitrile which was hydrogenated with 10% Pd/C until 3 equiv. of hydrogen were taken up. The catalyst was removed by filtration and the residue concentrated in vacuo to give a dark brown solid. Trituration with cold EtOH gave desired pure product.

N-(6-Chloro-3-cyanomethyl-1H-indol-5-yl)urea:

The method of Example 8 was applied to 5.0 g (0.024 mole) of the aminoindole above with 3.94 g (0.05 mole) KNCO to give after recrystallization twice from MeOH 4.74 g of desired urea.

N-[3-(2-Aminoethyl)-6-chloro-1H-indol-5-yl]urea:

A solution of 4.65 g (0.018 mole) of the nitrile above was reduced with RaNi as in Example 1 to give 3.91 g of a foamy oil. This oil was treated with 2.70 g of p-toluenesulfonic acid and the resultant salt recrystallized from EtOH to give 2.55 g of pure desired compound: m.p. 212°–213°.

Anal. Calcd for $C_{11}H_{13}ClN_4O \cdot C_1H_8O_3S$: C, 50.88; H, 4.98; N, 13.19; S, 7.55; Cl, 8.34. Found: C, 50.59; H, 5.17; N, 13.28; S, 7.18; Cl, 8.56.

EXAMPLE 15

N-[3-(2-Aminoethyl)-1H-indol-5-yl]acetamide (E)-2-Butenedioate (2:1)

N-[3-Cyanomethyl-1H-indol-5-yl]acetamide:

A solution of 6.0 g (0.035 mole) of 5-aminoindole-3-acetonitrile, Example 1, in 30 ml pyridine was treated with 15 ml of acetic anhydride. After stirring 18 hours, the solvent was removed in vacuo and residue recrystallized twice from EtOH to yield 4.35 g of product: m.p. 176°–177°.

Anal. Calcd for $C_{12}H_{11}N_3O$: C, 67.59; H, 5.20; N, 19.71. Found: C, 67.53; H, 5.27; N, 19.73.

N-[3-(2-Aminoethyl)-1H-indol-5-yl]acetamide:

The acetamidonitrile above (4.35 g, 0.02 mole) was reduced with RaNi as in Example 1 to give a gold oil, which was treated with 2.32 g (0.02 mole) of fumaric acid in EtOH. The resultant salt was filtered and recrystallized twice from EtOH/H$_2$O to afford 4.3 g of desired compound: m.p. 232°–234°.

Anal Calcd for $C_{12}H_{15}N_3O \cdot \frac{1}{2}Chd \ 4H_4O_4$: C, 61.08; H, 6.22; N, 15.26. Found: C, 61.06; H, 6.21; N, 15.34.

EXAMPLE 16

N-[3-(2-Aminoethyl)-1H-indol-5-yl]pyrrole-2-carboxamide 4-(Methylphenyl)sulfonate (1:1)

N-(3-Cyanomethyl-1H-indol-5-yl)pyrrole-2-carboxamide:

Phosgene was passed slowly into 50 ml THF until 4.46 g (0.045 mole) had been collected. To this solution was added 3.04 ml (0.844 mole) of pyrrole and the mixture stirred at 5° for 3 hours. The excess phosgene was driven off by heating and trapped in a NaOH trap to monitor CO$_2$ evolution. The reaction mixture was cooled, treated with 10 ml pyridine followed by a solution of 2.0 g (0.012 mole) of 5-aminoindole-3-acetonitrile, Example 1, in 50 ml THF and stirred 18 hours. Methanol was added to effect complete solution and 100 g silica gel added to adsorb desired product. The solvent was removed in vacuo and treated silica gel washed with 1.5 l of EtOAc which was then concentrated in vacuo to give crude product. This was further purified by column chromatography (EtOAc/Hexane (4:1) on silica gel) to give 1.16 g (37%) desired product: m.p. 216°–218°.

Anal. Calcd for $C_{15}H_{12}N_4O$: C, 68.17; H, 4.58; N, 21.20. Found: C, 67.88; H, 4.73; N, 20.92.

N-[3-(2-Aminoethyl)-1H-indol-5-yl]pyrrole-2-carboxamide:

The amidonitrile above (1.77 g, 0.007 mole) was reduced with RaNi as in Example 1 to give 1.51 g of an amorphous solid. This solid was dissolved in EtOH and treated with 1.14 g p-toluenesulfonic acid. The resultant precipitate was filtered and recrystallized from EtOH to give 2.06 g of pure product: m.p. 281°–283°.

Anal. Calcd for $C_{15}H_{16}N_4O \cdot C_7H_8O_3S$: C, 59.98; H, 5.49; N, 12.72; S, 7.28. Found: C, 59.85; H, 5.54; N, 12.57; S, 7.21.

Example 17

N-[3-(2-Aminoethyl)-1H-indol-5-yl]benzamide Methanesulfonate (1:1)

N-[3-Cyanomethyl-1H-indol-5-yl]benzamide:

A solution of 2.0 g (0.014 mole) of benzoyl chloride in THF was treated with 10 ml pyridine followed by 2.43 g (0.014 mole) of 5-aminoindole-3-acetonitrile, Example 1, and stirred 18 hr. The solvent was removed in vacuo and crude product recrystallized from EtOH to give product used directly in next step below.

N-[3-(2-Aminoethyl)-1H-indol-5-yl]benzamide:

The amide above (3.0 g, 0.011 mole) was reduced with RaNi as in Example 1 to give a crude beige solid which was dissolved in EtOH and treated with 1.05 g of methanesulfonic acid. The resultant salt was filtered and recrystallized twice from EtOH to give 1.70 g pure desired product: m.p. 259°–263°.

Anal. Calcd for $C_{17}H_{17}N_3O \cdot CH_4O_3S$: C, 57.58; H, 5.64; N, 11.19. Found: C, 57.38; H, 5.68; N, 10.95.

EXAMPLE 18

(1,1-Dimethylethyl) 1-{{N-[3-(2-Aminoethyl)-1H-indol-5-yl]amino}carbonyl}-2-phenylethylcarbamate 2-Naphthalenesulfonate (1:1)

(1,1-Dimethylethyl) 1-{[N-(3-cyanomethyl-1H-indol-5-yl)amino]carbonyl}-2-phenylethylcarbamate:

To a solution of 4.23 g (0.016 mole) of N-tBOC-phenylalanine in 300 ml acetone at 0°–5° was added 1.62 g (0.016 mole) of Et$_3$N and 1.75 g (0.016 mole) of ethyl chloroformate. The mixture was stirred at 0°–5° for $\frac{1}{2}$ hour after which 2.74 g (0.016 mole) of 5-aminoindole-3-acetonitrile, Example 1, in 50 ml acetone was added and the mixture stirred 18 hours. After filtration the filtrate was evaporated in vacuo to give a brown oil which was further purified by column chromatography (EtOAc/Hexane (2:1) on silica gel) and recrystallization from acetone/hexane to give 1.89 g (28% yield) of product: m.p. 146°–149°.

(1,1-Dimethylethyl) 1-{{N-[3-(2-Aminoethyl)-1H-indol-5-yl]amino}carbonyl}-2-phenyethylcarbamate:

The nitrile above (1.9 g, 0.005 mole) was reduced with RaNi as in Example 1 to give 1.83 g of a glassy solid which was dissolved in i-propyl alcohol and treated with 0.87 g 2-naphthalenesulfonic acid. Desired salt was filtered and recrystallized from acetonitrile to give 1.16 g of pure product: m.p. 204°–206°.

Anal. Calcd for $C_{24}H_{30}N_4O_3 \cdot C_{10}H_8O_3S$: C, 64.74; H, 6.07; N, 8.88; S, 5.08. Found: C, 64.34; H, 6.21; N, 8.76; S, 5.14

EXAMPLE 19

Ethyl N-[3-(2-Aminoethyl)-1H-indol-5-yl]carbamate Hydrochloride

Ethyl N-(3-Cyanomethyl-1H-indol-5-yl)carbamate:

This intermediate was prepared as in Example 17 using ethyl chloroformate.

Ethyl N-[3-(2-Aminoethyl)-1H-indol-5-yl]carbamate:

The RaNi reduction procedure of Example 1 was applied to the carbamate above (4.1 g, 0.017 mole) to give a crude oil. The oil was dissolved in EtOH and treated with ethereal HCl. On slow cooling a precipitate formed which was filtered, and after one additional recrystallization from EtOH afforded 2.50 g of desired product: m.p. 265°–267°.

Anal. Calcd for $C_{13}H_{17}N_3O_2 \cdot HCl$: C, 55.03; H, 6.39; N, 14.81 Found: C, 54.93; H, 6.47; N, 14.66.

EXAMPLE 20

N-[3-(2-Aminoethyl)-1H-indol-5-yl]pyridyl-2-carboxamide

N-(3-Cyanomethyl-1H-indol-5yl)pyridyl-2-carboxamide:

A solution of 2.0 g of picolinic acid chloride in THF is treated with 10 ml of pyridine followed by 2.42 g of 5-aminoindole-3-acetonitrile, Example 1, and stirred 18 hours. The solvent is removed in vacuo and product recrystallized from EtOH.

N-[3-(2-Aminoethyl)-1H-indol-5-yl]pyridyl-2-carboxamide:

The amide above is reduced with RaNi as in Example 1 to give a crude product which is dissolved in EtOH and treated with p-toluenesulfonic acid. The resultant precipitate is filtered and recrystallized from EtOH to give desired product.

The following examples illustrate various novel pharmaceutical compositions as typical procedures by which the novel compounds of the present invention may be administered:

EXAMPLE 21

1,000 hard gelatin capsules, each containing 200 milligrams of active ingredients e.g., N-[3-(2-aminoethyl)-1H-indol-5-yl]urea, or alternatively the title compounds of any of the foregoing examples, may be prepared from the following formulation:

|  | GRAMS |
| --- | --- |
| Active ingredient | 200 |
| Starch | 250 |
| Lactose | 750 |
| Talc | 250 |
| Calcium stearate | 10 |

A uniform mixture of the ingredients is prepared by blending and employed to fill two-piece hard gelatin capsules. The capsules are suitable to be orally administered to hypertensive subjects to reduce blood pressure.

EXAMPLE 22

1,000 compressed tablets, each containing 500 milligrams of active ingredients, may be prepared from the following formulation:

|  | GRAMS |
| --- | --- |
| Active ingredient | 500 |
| Starch | 100 |
| Microcrystalline cellulose | 100 |
| Calcium stearate | 2.5 |

The finely powdered ingredients are mixed well and granulated with 10 percent starch paste. The granulation is dried and compressed into tablets using starch as a disintegrant and calcium stearate as a lubricant.

We claim:

1. A method of treating hypertension in an animal comprising administering to the animal, a hypertension reducing amount of a pharmaceutical composition of a pharmaceutically-acceptable carrier and a 3-aminoalkyl-1H-indole-5-urea compound of the following formula (1):

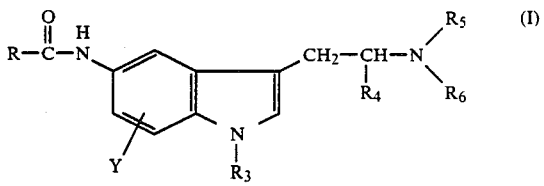

or a pharmaceutically acceptable acid addition salt thereof, wherein:
R is represented by $R_1R_2N-$;
$R_1$ is H, or $C_{1-4}$ loweralkyl, phenyl or cycloalkyl;
$R_2$ is H or a $C_{1-4}$ loweralkyl;
Y is H or halo;
$R_3$ is H or a $C_{1-4}$ loweralkyl;
$R_4$ is H or a $C_{1-4}$ loweralkyl;
$R_5$ is H, a $C_{1-4}$ loweralkyl, a $C_{1-4}$ loweralkylcarbonyl or $COCH_2CF_3$, and
$R_6$ is H or a $C_{1-4}$ loweralkyl; or
$R_5$ and $R_6$ are taken together as a N-loweralkylpyrrolidinylidene group.

2. N-[3-(2-aminoethyl)-1H-indol-5-yl]urea or a pharmaceutically acceptable acid addition salt thereof.

3. The method of claim 1, wherein in formula (I),
$R_1$ is H, methyl, phenyl or cyclohexyl;
$R_2$ is H or methyl;
$R_3$ is H or methyl,
$R_4$ is H;
$R_5$ is H or methyl;
$R_6$ is H or methyl; and
Y is H or chloro.

4. The method of claim 1, wherein said compound is N-[3-(2-aminoethyl)-1H-indol-5-yl]urea or a pharmaceutically-aceptable acid-addition salt thereof.

5. The method of claim 1, wherein said compound is N-[3-(2-aminoethyl)-1H-indol-5-yl]-N'-cyclohexylurea or a pharmaceutically-acceptable acid-addition salt thereof.

6. The method of claim 1, wherein said compound is N-[3-(2-aminoethyl)-1H-indol-5-yl]-N'-phenylurea or a pharmaceutically-acceptable acid-addition salt thereof.

7. The method of claim 1, wherein said compound is N-[3-(2-aminoethyl)-1H-indol-5-yl]-N'-methyl urea or a pharmaceutically-acceptable acid-addition salt thereof.

8. The method of claim 1, wherein said compound is N-[3-(2-aminoethyl)1H-indol-5-yl]-N',N'-dimethyl urea or a pharmaceutically-acceptable acid-addition salt thereof.

9. The method of claim 1, wherein said compound is N-[3-(2-dimethylaminoethyl)-1H-indol-5-yl]urea or a pharmaceutically-acceptable acid-addition salt thereof.

10. The method of claim 1, wherein said compound is
N-[3-(2-aminoethyl)-1H-indol-5-yl]urea,
N-[3-(2-aminoethyl)-1H-indol-5-yl]-N'-cyclohexylurea,
N-[3-(2-aminoethyl)-1H-indol-5-yl]-N'-phenylurea,
N-[3-(2-aminoethyl)-1H-indol-5-yl]-N'-methylurea,
N-[3-(2-aminoethyl)-1H-indol-5-yl]-N',N'-dimethylurea,
N-[3-(2-dimethylaminoethyl)-1H-indol-5-yl]urea,
N-[3-(2-methylaminoethyl)-1H-indol-5-yl]urea,
N-[3-(2-methylethylaminoethyl)-1H-indol-5-yl]urea,
N-[3-{2-[N-(1-methyl-2-pyrrolidinylidene)]ethylamine}-1H-indol-5-yl]urea,
N-[3(2-aminopropyl)-1H-indol-5-yl]urea,
N-[3-(2-aminoethyl)-1-methyl-1H-indol-5-yl]urea, or
N-[3-(2-aminoethyl)-6-chloro-1H-indol-5-yl]urea,
or a pharmaceutically-acceptable acid-addition salt thereof.

11. N-[3-(2-Aminoethyl)-1H-indol-5-yl]urea.

* * * * *